(12) United States Patent
Catanzarite et al.

(10) Patent No.: US 9,474,539 B2
(45) Date of Patent: Oct. 25, 2016

(54) PATIENT-SPECIFIC CONVERTIBLE GUIDES

(71) Applicant: Biomet Manufacturing, LLC, Warsaw, IN (US)

(72) Inventors: Joshua B. Catanzarite, Warsaw, IN (US); Ryan J. Schoenefeld, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 417 days.

(21) Appl. No.: 14/200,990

(22) Filed: Mar. 7, 2014

(65) Prior Publication Data

US 2014/0188119 A1    Jul. 3, 2014

Related U.S. Application Data

(62) Division of application No. 13/097,145, filed on Apr. 29, 2011, now Pat. No. 8,668,700.

(51) Int. Cl.
*A61B 17/17* (2006.01)
*A61B 17/15* (2006.01)
*A61B 17/56* (2006.01)

(52) U.S. Cl.
CPC ......... *A61B 17/1764* (2013.01); *A61B 17/155* (2013.01); *A61B 2017/568* (2013.01)

(58) Field of Classification Search
CPC .................... A61B 17/1764; A61B 2017/568
See application file for complete search history.

(56) References Cited

U.S. PATENT DOCUMENTS

| 1,480,285 A | 1/1924 | Moore |
| 2,181,746 A | 11/1939 | Siebrandt |
| 2,407,845 A | 9/1946 | Nemeyer |

(Continued)

FOREIGN PATENT DOCUMENTS

| CA | 2447694 A1 | 12/2002 |
| CA | 2501041 A1 | 4/2004 |

(Continued)

OTHER PUBLICATIONS

European Communication Pursuant to Article 94(3) EPC mailed Jan. 22, 2015 for PCT/US2007/013223 filed Jun. 5, 2007, which claims benefit of U.S. Appl. No. 60/812,694, filed Jun. 9, 2006 and U.S. Appl. No. 11/756,057, filed May 31, 2007.

(Continued)

*Primary Examiner* — David Bates
(74) *Attorney, Agent, or Firm* — Schwegman Lundberg & Woessner, P.A.

(57) ABSTRACT

A method of intraoperatively selecting between a partial knee arthroplasty and total knee arthroplasty includes mounting a patient-specific three-dimensional surface of a convertible patient-specific guide in a unique position mating to a corresponding surface of a distal femoral bone. The convertible patient-specific guide includes an anterior portion and a distal portion a patellofemoral guide. One of a total knee arthroplasty and a partial knee arthroplasty is selected intraoperatively. If total knee arthroplasty is selected, first and second covers are removed from corresponding first and second distal guiding bore. First and second distal pins through the first and second distal guiding bores are registered on the bone. If partial knee arthroplasty is selected, the anterior portion is severed and removed along a frangible groove and the distal portion is used as a patellofemoral guide.

20 Claims, 7 Drawing Sheets

(56) References Cited

U.S. PATENT DOCUMENTS

| | | |
|---|---|---|
| 2,416,228 A | 2/1947 | Sheppard |
| 2,618,913 A | 11/1952 | Plancon et al. |
| 2,910,978 A | 11/1959 | Urist |
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,528,980 A | 7/1985 | Kenna |
| 4,565,191 A | 1/1986 | Slocum |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,006,121 A | 4/1991 | Hafeli |
| 5,007,936 A | 4/1991 | Woolson |
| 5,030,219 A | 7/1991 | Matsen, III et al. |
| 5,030,221 A | 7/1991 | Buechel et al. |
| 5,041,117 A | 8/1991 | Engelhardt |
| 5,053,037 A | 10/1991 | Lackey |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,593,411 A | 1/1997 | Stalcup et al. |
| 5,595,703 A | 1/1997 | Swaelens et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliott et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |

(56) References Cited

U.S. PATENT DOCUMENTS

| | | |
|---|---|---|
| 5,766,251 A | 6/1998 | Koshino et al. |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,008,433 A | 12/1999 | Stone |
| 6,019,767 A | 2/2000 | Howell |
| 6,033,415 A | 3/2000 | Mittelstadt et al. |
| 6,042,612 A | 3/2000 | Voydeville |
| 6,056,754 A | 5/2000 | Haines et al. |
| 6,059,789 A | 5/2000 | Dinger et al. |
| 6,059,833 A | 5/2000 | Doets |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 | 12/2001 | Franklin et al. |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,424,332 B1 | 7/2002 | Powell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,610,067 B2 | 8/2003 | Tallarida et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |

(56) References Cited

U.S. PATENT DOCUMENTS

| | | |
|---|---|---|
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Buttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'Neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,690 B2 | 11/2010 | Metzger |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Rossner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'Neill et al. |
| 8,268,100 B2 | 9/2012 | O'Neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |

(56) References Cited

U.S. PATENT DOCUMENTS

| | | |
|---|---|---|
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite et al. |
| 8,979,936 B2 | 3/2015 | White et al. |
| 9,005,297 B2 | 4/2015 | Katrana et al. |
| 2001/0005797 A1 | 6/2001 | Barlow et al. |
| 2001/0011190 A1 | 8/2001 | Park |
| 2001/0021876 A1 | 9/2001 | Terrill-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |

(56) References Cited

U.S. PATENT DOCUMENTS

| | | |
|---|---|---|
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |

(56) References Cited

U.S. PATENT DOCUMENTS

| | | |
|---|---|---|
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |

(56) References Cited

U.S. PATENT DOCUMENTS

| | | |
|---|---|---|
| 2011/0029093 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-Scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0192401 A1 | 8/2012 | Pavlovskaia et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'Neill et al. |
| 2013/0060253 A1 | 3/2013 | Couture et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger et al. |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman et al. |
| 2013/0264749 A1 | 10/2013 | Jones et al. |
| 2013/0268085 A1 | 10/2013 | Dong et al. |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, III et al. |
| 2014/0081275 A1 | 3/2014 | Metzger et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1 | 5/2014 | Maxson et al. |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |

(56) References Cited

U.S. PATENT DOCUMENTS

| | | |
|---|---|---|
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 3447365 A1 | 7/1986 |
| DE | 04219939 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6-233790 A | 8/1994 |
| JP | 2000245758 A | 9/2000 |
| JP | 2005-218861 A | 8/2005 |
| JP | 2009514612 A | 4/2009 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 | 5/2005 |
| TW | 201114409 A | 5/2011 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011080260 A1 | 7/2011 |

(56) References Cited

FOREIGN PATENT DOCUMENTS

| WO | WO-2011106711 A1 | 9/2011 |
|----|------------------|--------|
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |
| WO | WO-2013170872 A1 | 11/2013 |
| WO | WO-2014019712 A1 | 2/2014 |

OTHER PUBLICATIONS

European Communication Pursuant to Article 94(3) EPC mailed Feb. 4, 2015 for PCT/US2010/024584 filed Feb. 18, 2010, which claims benefit of U.S. Appl. No. 12/389,901, filed Feb. 20, 2009.

European Communication Pursuant to Article 94(3) EPC mailed Feb. 10, 2015 for PCT/US2009/039507 filed Apr. 3, 2009, which claims benefit of U.S. Appl. No. 12/103,824, filed Apr. 16, 2008.

International Preliminary Report on Patentability and Written Opinion mailed on Mar. 12, 2015 for PCT/US2013/057097 claiming benefit of U.S. Appl. No. 13/597,478, filed Aug. 29, 2012.

Japanese Office Action mailed on Apr. 7, 2015 for PCT/US2012/038351 filed May 17, 2012 claiming benefit of U.S. Appl. No. 13/111,007, filed May 19, 2011.

Patent Examiniation Report No. 1 mailed Feb. 16, 2015 for PCT/US2013/026875 filed Feb. 20, 2013, which claims benefit of U.S. Appl. No. 13/400,652, filed Feb. 21, 2012.

Signature™ Hip Technology Personalized Patient Care brochure. Biomet® Orthopedics. (2013) (8 pages).

Signature™ Personalized Patient Care. Surgical Technique Acetabular Guide System brochure. Biomet® Orthopedics. (2013) pp. 1-13.

International Preliminary Report on Patentability Report and Written Opinion mailed Sep. 4, 2014 for PCT/US2013/026875 claiming benefit of U.S. Appl. No. 13/400,652, filed Feb. 21, 2012.

International Search Report and Written Opinion mailed Jul. 10, 2014 for PCT/US2014/023655 claiming benefit of U.S. Appl. No. 13/800,369, filed Mar. 13, 2013.

European Communication Pursuant to Article 94(3) EPC mailed Nov. 24, 2014 for PCT/US2012/038351 which claims benefit of U.S. Appl. No. 13/111,007, filed May 19, 2011.

Farr, J., Cole, B. , Kercher, J., Batty, L. and Bajaj, S., Anteromedial Tibial Tubercle Osteotomy (Fulkerson Osteotomy). Re-print from V. Sanchis-Alfonso (ed), Anterior Knee Pain and patellar Instability, DOI: 10.1007/978-0-85729-507-1_40, © Springer-Verlag London Limited 2011.(9 pages).

Farr, J., Fulkerson, J. Surgical Technique for Anteromedialization of the Tibial Tubercle with the Tracker™ AMZ Guide System. Sports Medicine and Arthroscopy Review, vol. 2, No. 3, 1994. (12 pages).

"Is Subchondroplasty® Right for Me?" Retrieved from <http://www.subchondroplasty.com/about_subchondroplasty/is_subchondroplasty_right_for_>. . . Jul. 1, 2013. 1 sheet.

"Subchondroplasty," Retrieved from <http://www.subchondroplasty.com/>. Jul. 1, 2013. 1 sheet.

Deakon, Timothy, MD, Posterior Cruciate Ligament Reconstruction Technique Using the Modular ACL/PCL Guide Rationale and Surgical Technique, Arthrotek®, a Biomet Company. (2003). (6 pages).

International Preliminary Report on Patentability and Written Opinion mailed May 8, 2014 for PCT/US2012/060842 claiming benefit of U.S. Appl. No. 13/653,868, filed Oct. 17, 2012.

International Preliminary Report on Patentability and Written Opinion mailed May 8, 2014 for PCT/US2012/060848 claiming benefit of U.S. Appl. No. 13/653,878, filed Oct. 17, 2012.

International Preliminary Report on Patentability and Written Opinion mailed May 8, 2014 for PCT/US2012/060853 claiming benefit of U.S. Appl. No. 13/653,886, filed Oct. 17, 2012.

International Preliminary Report on Patentability and Written Opinion mailed May 8, 2014 for PCT/US2012/060854 claiming benefit of U.S. Appl. No. 13/653,893, filed Oct. 17, 2012.

International Search Report and Written Opinion mailed Jun. 24, 2014 for PCT/US2014/022000 claiming benefit of U.S. Appl. No. 13/889,869, filed May 8, 2013.

International Search Report and Written Opinion mailed May 23, 2014 for PCT/US2013/074288 claiming benefit of U.S. Appl. No. 13/790,770, filed Mar. 8, 2013, which priority is also claimed of U.S. Appl. No. 13/711,306, filed Dec. 11, 2012.

What is Subchondroplasty, Retrieved from <http://www.subchondroplasty.com/about_subchondroplasty/what_is_subchondroplasty.>, Jul. 1, 2013. 2 sheets.

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (Oct. 31, 1999) 16 sheets.

"Comprehensive® Reverse Shoulder System Surgical Technique," Biomet Orthopedics brochure (2009-2012), 48 pages.

"Comprehensive® Reverse Shoulder System Technical Design Features," Biomet Orthopedics brochure (2009), 3 pages.

"Comprehensive® Reverse Shoulder System," Biomet Orthopedics brochure (2009), 8 pages.

"Comprehensive® Shoulder System Surgical Technique," Biomet Orthopedics brochure (2007), pp. 1-53.

"Comprehensive® Total Shoulder System," Biomet Orthopedics brochure (2011), 4 pages.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (Dec. 31, 2008) pp. 1-25.

"Discovery® Elbow System," brochure. Biomet Orthopedics, Inc. (Nov. 30, 2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (Mar. 31, 2004) pp. 1-8 (12 sheets).

"Patient Matched PMI Implants, C.A.M.R.A. 3-D Imaging," brochure, Biomet, Inc. (Jan. 31, 1991) 6 pages.

"Regenerex® Tibial Cone Augment, Surgical Technique Addendum to the Vanguard® SSK Revision System," brochure. Biomet® Orthopedics. (Mar. 31, 2010) pp. 1-8 (12 sheets).

"Signature™ Personalized Patient Care, Surgical Technique Addendum to the Vanguard Knee System" brochure. Biomet® Orthopedics, Inc. (May 15, 2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (Aug. 31, 2010) pp. 1-25.

"Zimmer® UniSpacer® Knee System," brochure. (2005) Zimmer, Inc. 4 sheets.

Biomet "Oxford® Partial Knee" brochure, 8 pages (Feb. 2011).

Biomet "The Oxford® Partial Knee Surgical Technique," brochure, pp. 1-38, (Feb. 2010).

(56) References Cited

OTHER PUBLICATIONS

Biomet, "Oxford® Partial Knee Microplasty® Instrumentation Surgical Technique", brochure, pp. 1-54 (May 2011).
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Friedman, R.J. et al., "The Use of Computerized Tomography in the Measurement of Glenoid Version", Journal of Bone & Joint Surgery Am. (JBJS) 1992;74:1032-1037 (Aug. 1992).
Great Britain Search Report mailed Dec. 21, 2011 for GB1116054.6, claiming benefit of U.S. Appl. No. 12/888,005, filed Sep. 22, 2010.
Haaker, R.G., et al., "Minimal-invasive navigiert implantierte unikondyläre Knieendoprothese," Orthopäde 2006 35:1073-1079 (Sep. 13, 2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report and Written Opinion mailed Jan. 5, 2012 for PCT/US2010/038845 claiming benefit of U.S. Appl. No. 12/486,992, filed Jun. 18, 2009.
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Apr. 24, 2014 for PCT/US2012/059189 claiming benefit of U.S. Appl. No. 13/597,478, filed Aug. 29, 2012.
International Preliminary Report on Patentability and Written Opinion mailed Dec. 22, 2011 for PCT/US2010/038177 claiming benefit of U.S. Appl. No. 12/483,807, filed Jun. 12, 2009.
International Preliminary Report on Patentability and Written Opinion mailed Jan. 3, 2014 for PCT/US2012/042081 claiming benefit of U.S. Appl. No. 13/493,509, filed Jun. 11, 2012.
International Preliminary Report on Patentability and Written Opinion mailed Mar. 13, 2014 for PCT/US2012/052853 claiming benefit of U.S. Appl. No. 13/221,968, filed Aug. 31, 2011.
International Preliminary Report on Patentability and Written Opinion mailed Nov. 28, 2013 for PCT/US2012/038351 claiming benefit of U.S. Appl. No. 13/111,007, filed May 19, 2011.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability and Written Opinion mailed Sep. 7, 2012 for PCT/US2011/026333 claiming benefit of U.S. Appl. No. 12/714,023, filed Feb. 26, 2010.
International Preliminary Report on Patentability for PCT/US2007/013223 mailed Dec. 24, 2008 claiming benefit of U.S. Appl. No. 11/756057, filed May 31, 2007.
International Preliminary Report on Patentability for PCT/US2010/050701 mailed Apr. 12, 2012 claiming benefit of U.S. Appl. No. 12/571,969, filed Oct. 1, 2009.
International Preliminary Report on Patentability mailed Aug. 25, 2011 for PCT/US2010/024073 filed Feb. 12, 2010, claiming benefit of U.S. Appl. No. 12/371,096, filed Feb. 13, 2009.
International Preliminary Report on Patentability mailed Mar. 31, 2011 for PCT/US2009/056670 claiming benefit of U.S. Appl. No. 12/211,407, filed Sep. 16, 2008.
International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Preliminary Report on Patentability mailed Sep. 6, 2013 for PCT/US2012/026356 claiming benefit of U.S. Appl. No. 13/041,883, filed Mar. 7, 2011.
International Search Report and Written Opinion for PCT/US2007/013223 mailed Nov. 26, 2007, claiming benefit of U.S. Appl. No. 11/756057, filed May 31, 2007.
International Search Report and Written Opinion for PCT/US2009/039507 mailed Jul. 14, 2009, claiming benefit of U.S. Appl. No. 12/103824, filed Apr. 16, 2008.
International Search Report and Written Opinion for PCT/US2009/056670 mailed Mar. 2, 2010 claiming benefit of U.S. Appl. No. 12/211,407, filed Sep. 16, 2008.
International Search Report and Written Opinion for PCT/US2013/026875 mailed Jun. 7, 2013, claiming benefit of U.S. Appl. No. 13/400,652, filed Feb. 21, 2012.
International Search Report and Written Opinion mailed Apr. 14, 2014 for PCT/US2013/067505 claiming benefit of U.S. Appl. No. 13/718,129, filed Dec. 18, 2012.
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Aug. 24, 2010 for PCT/US2010/038177 claiming benefit of U.S. Appl. No. 12/483,807, filed Jun. 12, 2009.
International Search Report and Written Opinion mailed Aug. 9, 2011 for PCT/US2011/026333 claiming benefit of U.S. Appl. No. 12/714,023, filed Feb. 26, 2010.
International Search Report and Written Opinion mailed Dec. 18, 2012 for PCT/US2012/059189, which claims benefit of U.S. Appl. No. 13/597,478, filed Aug. 29, 2011.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Feb. 6, 2013 for PCT/US2012/060842, which claims benefit of U.S. Appl. No. 13/653,868, filed Oct. 17, 2012.
International Search Report and Written Opinion mailed Feb. 6, 2013 for PCT/US2012/060854, which claims benefit of U.S. Appl. No. 13/653,893, filed Oct. 17, 2012.
International Search Report and Written Opinion mailed Jul. 31, 2009 for PCT/US2009/039578 claiming benefit of U.S. Appl. No. 12/103,834, filed Apr. 16, 2008.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed Mar. 5, 2012 for PCT/US2011/057300 claiming benefit of U.S. Appl. No. 12/938,905, filed Nov. 3, 2010.
International Search Report and Written Opinion mailed May 8, 2012 for PCT/US2012/026356 claiming benefit of U.S. Appl. No. 13/041,883, filed Mar. 7, 2011.

(56) References Cited

OTHER PUBLICATIONS

International Search Report and Written Opinion mailed May 9, 2011 for PCT/US2011/026412 claiming benefit of U.S. Appl. No. 12/872,663, filed Aug. 31, 2010.
International Search Report and Written Opinion mailed Nov. 15, 2012, for PCT/US2012/052853, which claims benefit of U.S. Appl. No. 13/221,968, filed Aug. 31, 2011.
International Search Report and Written Opinion mailed Oct. 14, 2013 for PCT/US2013/057097 claiming benefit of U.S. Appl. No. 13/597,478, filed Aug. 29, 2012.
International Search Report and Written Opinion mailed Oct. 5, 2010 for PCT/US2010/038845 claiming benefit of U.S. Appl. No. 12/486,992, filed Jun. 18, 2009.
International Search Report mailed Nov. 30, 2010 for PCT/EP2010/061630 filed Aug. 10, 2010 claiming benefit of DE102009028503.2 filed Aug. 13, 2009.
International Search Report mailed Oct. 23, 2012, for PCT/US2012/041893, which claims benefit of U.S. Appl. No. 61/496,177, filed Jun. 13, 2011.
Invitation to Pay Additional Fees mailed Feb. 6, 2013 for PCT/US2012/060848, which claims benefit of U.S. Appl. No. 13/653,878, filed Oct. 17, 2012.
Invitation to Pay Additional Fees mailed Feb. 6, 2014 for PCT/US2013/067505, which claims benefit of U.S. Appl. No. 13/718,129, filed Dec. 18, 2012.
Invitation to Pay Additional Fees mailed Feb. 7, 2013 for PCT/US2012/060853, which claims benefit of U.S. Appl. No. 13/653,893, filed Oct. 17, 2012.
Invitation to Pay Additional Fees mailed May 3, 2011 for PCT/US2011/026333 claiming benefit of U.S. Appl. No. 12/714,023, filed Feb. 26, 2010.
Invitation to Pay Additional Fees with Partial International Search mailed Nov. 26, 2009 for PCT/US2009/056670.
K. Subburaj et al., "Automated 3D Geometric Reasoning in Computer Assisted Joint Reconstructive Surgery", IEEE International Conference on Automation Science and Engineering, Publication Year: 2009, pp. 367-372.
Kaus, Michael R., Ph.D., "Automated Segmentation of Mr Images of Brain Tumors," Radiology, vol. 218, No. 2, (2001) pp. 586-591.
Kelly, Todd C., M.D., "Role of Navigation in Total Hip Arthroplasty." The Journal of Bone & Joint Surgery(2009) pp. 153-8. vol. 91-A, Supplement 1.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 (pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Radermacher, Klaus, et al. "Computer Assisted Orthopaedic Individual Templates." Clinical Orthopaedics and Related Research. (Sep. 1998) No. 354; pp. 28-38.
Schuller-Götzburg, P., et al., 3D-Implantatplanung und Stereolithographie-Implantatbohrschablonen, Stomatologie 101.3, pp. 55-59 (May 2004).
Sharp, S. Michael, Ph.D., Patient-Specific, Resurfacing Bi-Compartmental Arthuroplasty, Futuretech, Orthopaedic Product News (Mar./Apr. 2008) pp. 12-15.
Signature™ Personalized Patient Care, Surgical Technique Addendum Vanguard® Complete Knee System, Biomet® Orthopedics Brochure, (2011), p. 1-32.
Sisto, Domenick, J., et al., "Custom Patellofemoral Arthroplasty of the Knee Surgical Technique," Journal of Bone and Joint Surgery, vol. 89-A, pp. 214-225 (Jul. 2006).
Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.
Steinwachs, Matthias Reinhard, "Cartilage Repair—Autologous Chondrocyte Transplantation and Autologous Matrix-induced Chondrogenesis," European Musculoskeletal Review (2006) pp. 65-68.
Supplementary European Search Report mailed Nov. 15, 2011 for EP07809326, which claims benefit of PCT/US2007/013223, filed Jun. 5, 2007; which claims benefit of U.S. Appl. No. 11/756,057, filed May 31, 2007.
Thomas, W., et al., "Endoprothetischen Versorgung des Kniegelenks auf der Basis eines 3D-computertomographischen Subtraktionversfahrens," Zuma Thema: Computergestützte orthopädische Chirugie, Der Orthopäde 29:641-644 Springer-Verlag (Jul. 2000) Translation provided: Thomas, W., "Endoprosthetic care of the knee joint based on a 3D computer chromatography subtraction process," Topic: Computer-aided orthopedic surgery. Orthopedist 2000 29:641-644 Springer Verlag (Jul. 2000).

PATIENT-SPECIFIC CONVERTIBLE GUIDES

CROSS-REFERENCE TO RELATED APPLICATIONS

This application is a divisional of U.S. application Ser. No. 13/097,145 filed on Apr. 29, 2011. The disclosure of the above application is incorporated herein by reference.

FIELD

The present teachings relate to patient-specific guides for orthopedic surgery and in particular to patient-specific guides that are convertible to accommodate intraoperative changes of a preoperative surgical plan for a patient.

INTRODUCTION

The present teachings relate to devices and methods for enabling the surgeon to change a preoperative surgical plan for a specific patient intraoperatively from a first surgical procedure to a second surgical procedure without requiring separate patient-specific guides that are individually dedicated to each procedure. For example, the preoperative plan for the patient may be designed for a partial knee arthroplasty, but intraoperatively, the surgeon may make a determination to perform a total knee arthroplasty. The present disclosure provides various exemplary guides for allowing the surgeon to convert from one surgical procedure to another intraoperatively with efficiency, ease and cost effectiveness.

SUMMARY

This section provides a general summary of the disclosure, and is not a comprehensive disclosure of its full scope or all of its features.

The present teachings provide a convertible patient-specific guide for use in arthroplasty. The convertible guide has a body having a patient-specific three-dimensional undersurface closely mateable in only one position with a corresponding joint surface of a specific patient. The convertible guide includes patient-specific guiding formations extending from the body and configured for guiding both a total arthroplasty of the joint and a partial arthroplasty of the joint, such that the arthroplasty to be performed is intraoperatively changeable.

The present teachings also provide a convertible patient-specific guide that includes a body having a patient-specific three-dimensional undersurface closely mateable in only one position with a corresponding femoral knee joint surface of a specific patient. The convertible patient-specific guide includes patient-specific guiding formations extending from the body and configured for guiding a total knee arthroplasty of the joint. The convertible patient-specific guide further includes a connector extending from the body. The connector can be coupled with a patient-specific unicondylar knee guide for intraoperatively converting a unicondylar partial knee arthroplasty to a total knee arthroplasty.

The present teachings provide a method of intraoperatively selecting between a partial knee arthroplasty and total knee arthroplasty. The method includes mounting a patient-specific three-dimensional surface of a patient-specific guide in a unique position mating to a corresponding surface of a distal femoral bone. The patient-specific guide includes an anterior portion and a distal portion including a patellofemoral guide portion. The method includes selecting one of a total knee arthroplasty and a partial knee arthroplasty. If total knee arthroplasty is selected, first and second covers are removed from corresponding first and second distal guiding bores and first and second distal pins are registered through the first and second distal guiding bores. If partial knee arthroplasty is selected, the anterior portion is removed along a frangible groove and the patellofemoral guide portion for partial knee arthroplasty.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
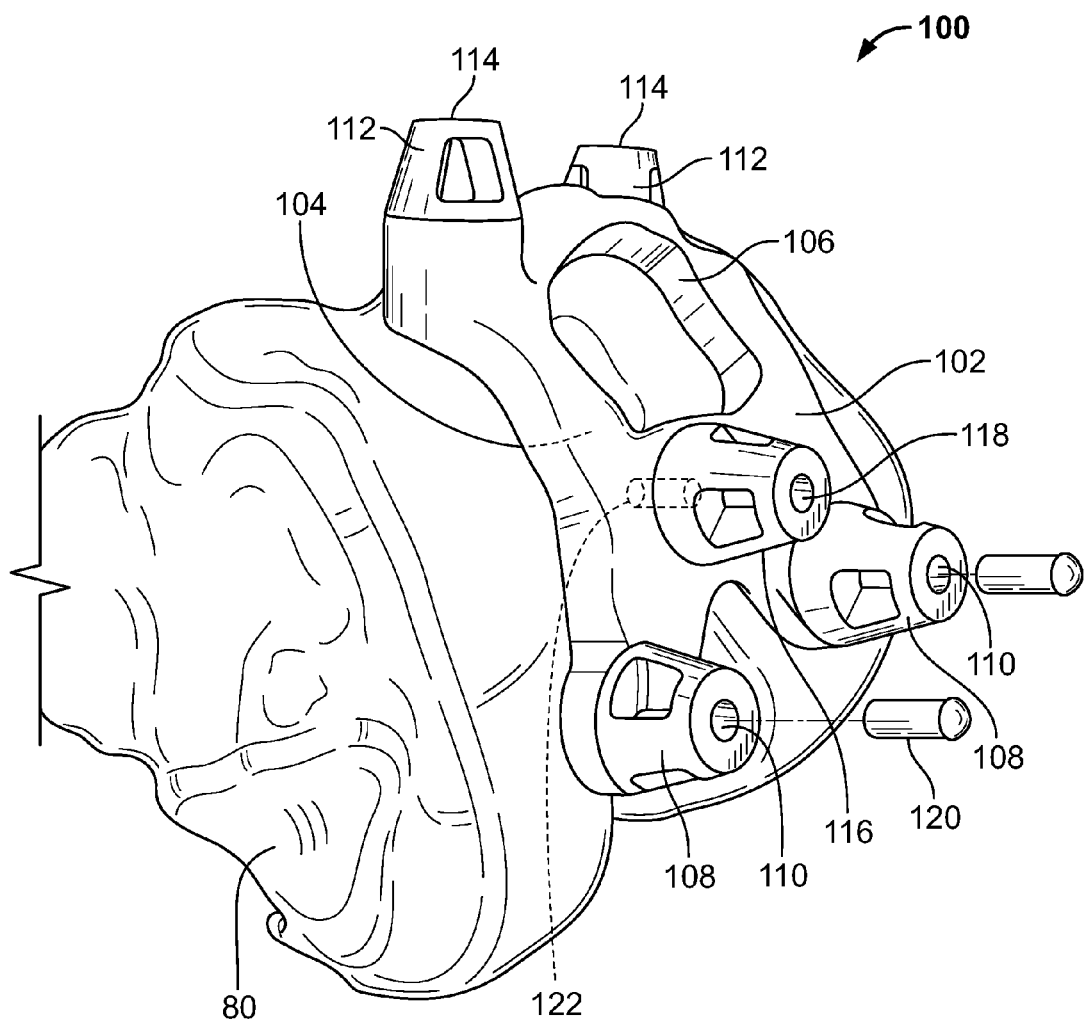
FIG. 1 is an environmental view of a patient-specific convertible guide selectively usable either for a total knee arthroplasty or a patellofemoral procedure as determined intraoperatively by the surgeon according to the present teachings.

Exemplary embodiments will now be described more fully with reference to the accompanying drawings.

The present teachings generally provide various patient-specific or custom guides and/or other instruments and devices for total and/or partial arthroplasty including unicondylar knee arthroplasty and patellofemoral compartment arthroplasty. More specifically, the present teachings provide various customized and patient-specific guides and other devices that enable the surgeon to change a preoperative surgical plan for a specific patient intraoperatively from a first surgical procedure to a second surgical procedure without requiring separate patient-specific guides dedicated to each procedure. For example, preoperatively, a partial knee arthroplasty (PKA) may have been contemplated for a specific patient, but intraoperatively observed conditions may lead the surgeon to perform a total knee arthroplasty (TKA) instead.

The present teachings provide various exemplary guides, devices and methods for allowing the surgeon to convert from one surgical procedure to another intraoperatively while maintaining the benefit of a preoperative plan and the use of patient-specific guides. In some embodiments, for example, a single patient-specific guide can be a dual purpose/dual function guide that can provide alignment guidance for both TKA and PKA procedures. In some embodiments, a single patient-specific guide can be convertible from one procedure to another. Unless there is a need to distinguish between particular embodiments, patient-specific guides designed for dual surgical procedures or convertible from one surgical procedure to another intraoperatively will be referenced as "convertible" guides. Patient-specific convertible guides are described below in further detail, although non-custom convertible guides can also be used.

The patient-specific convertible guides and other associated instruments and devices can be used either with patient-specific or with conventional/standard (i.e., non-custom) femoral or tibial implant components. Generally, patient-specific devices can be designed preoperatively using computer-assisted image methods based on three-dimensional images of the patient's knee anatomy reconstructed from MRI, CT, ultrasound, X-ray, or other three- or two-dimensional medical scans of the patient's anatomy and in some cases complemented with digital photography methods and/or anthropometry databases. Various CAD programs and/or software can be utilized for three-dimensional image reconstruction, such as software commercially available, for example, by Materialise USA, Plymouth, Mich.

In the preoperative planning stage for a joint replacement or revision procedure, such as, for example, total knee arthroplasty (TKA) or partial knee arthroplasty (PKA), or patellofemoral compartment (PFR) arthroplasty, imaging data of the relevant anatomy of a patient can be obtained at a medical facility or doctor's office, using one of medical imaging methods described above. The imaging data can include, for example, various medical scans of a hip, knee, ankle or other joint or relevant portion of the patient's anatomy, as needed for joint modeling, mechanical/alignment axis determination or for other alignment purposes. The imaging data obtained and other associated information can be used to construct a three-dimensional computer image of the joint or other portion of the anatomy of the patient. An initial preoperative plan can be prepared for the patient in image space and can include bone or joint preparation, planning for resections, milling, reaming, broaching, implant selection and fitting, as well as designing patient-specific guides, templates, tools and alignment methods for the surgical procedure.

In the context of the present teachings, patient-specific guides and implants are generally configured to match the anatomy of a specific patient and are generally formed using computer modeling based on the patient's reconstructed three-dimensional anatomic image. The patient-specific guides have an engagement surface that is made to conformingly contact and match a three-dimensional image/model of the patient's bone surface (with or without cartilage or other soft tissue), by the computer methods discussed above. In this respect, a patient-specific guide can nestingly mate with the corresponding bone surface (with or without articular cartilage) of the specific patient in only one position. The patient-specific alignment guides can include custom-made (patient-specific) guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan.

The customization of the guiding formations is designed during the preoperative plan to provide templates for guiding cutting tools to perform the planned drilling, resections or other surface preparation according to the preoperative plan. For example, the guiding formations can provide spatial orientation and positions for drilling of holes to insert pins or other supporting connectors for mounting the corresponding cutting tools for the preparation of the bone. The patient-specific guides can be used in minimally invasive surgery, and also in surgery with multiple minimally-invasive incisions. Various alignment guides and pre-operative planning procedures are disclosed in commonly assigned and co-pending U.S. patent application Ser. No. 11/756,057, filed on May 31, 2007, U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; U.S. patent application Ser. No. 12/025,414, filed Feb. 4, 2008, U.S. patent application Ser. No. 12/571,969, filed Oct. 1, 2009, and U.S. patent application Ser. No. 12/955,361, filed Nov. 29, 2010. The disclosures of the above applications are incorporated herein by reference.

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer file form associated with interactive software, can be sent or otherwise provided over the internet or other cloud/web type of communication to the surgeon, or other medical practitioner, for review. The surgeon can incrementally manipulate the position of images of the implant components in an interactive image of the joint. Additionally, the surgeon can select or modify resection planes, types of implants and orientation and position of implant insertion. After the surgeon modifies and/or approves the surgical plan, the surgeon can send or electronically communicate or save in an internet space or dedicated server the final, approved preoperative plan that can be accessed by the manufacturer. Patient-specific guides and other tools for the approved preoperative plan can be manufactured and included with the selected implants and other instruments or devices in a kit for the specific patient, specific procedure and specific surgeon. In addition, patient-specific physical models of the corresponding bone portions can be prepared for physical visualization and trial testing of the bone, as discussed below. The various patient-specific guides discussed herein can be made of any biocompatible material, including metal or plastic. Generally, the patient-specific guides are disposable and made of lightweight materials, including polymers.

Figure 1A:
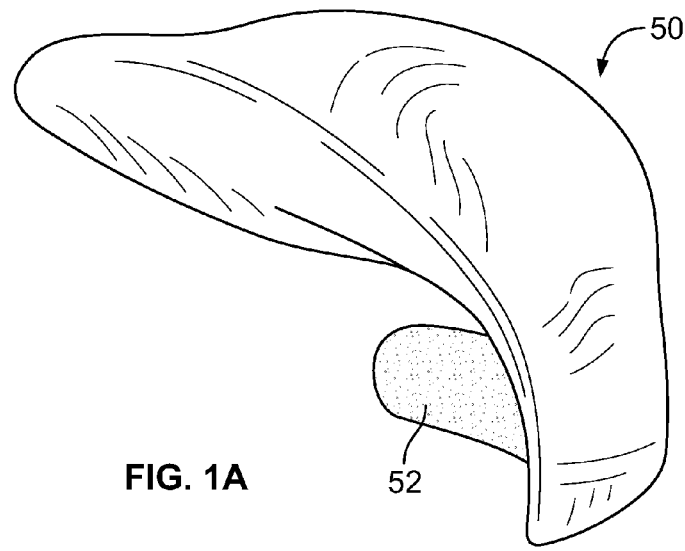
FIG. 1A is a perspective view of an exemplary patellofemoral implant.

Referring to FIG. 1, an exemplary dual purpose, ("convertible" for short) patient-specific guide 100 is shown mounted on the corresponding patient's distal femur 80. The convertible guide 100 includes a light-weight body 102 having an inner or anatomy engaging surface 104 that is designed during the preoperative plan of the patient to be patient-specific, i.e., to nestingly mate with the patient's joint surface, such as portions of the anterior and distal surfaces of the patient's femur 80 (with or without articular cartilage) in only one position, as determined by the preoperative plan. The convertible guide 100 can include a visualization window/opening 106 and first and second distal guiding formations 108 defining distal guiding bores 110 for guiding corresponding distal alignment pins (not shown). The convertible guide 100 can also include first and second anterior guiding formations 112 defining anterior guiding bores 114 for guiding corresponding anterior alignment pins (not shown). The distal and anterior guiding formations 108, 112 are designed to have orientations and positions for guiding pins or other connecting members on which to support various cutting instruments to perform the resections determined in a preoperative plan for an optional total knee arthroplasty. A fifth patellofemoral guiding formation 116 having a patellofemoral guiding bore 118 is also provided on the convertible guide 100 for guiding an optional partial knee replacement, such as a patellofemoral replacement in which a patellofemoral replacement system is used, such as, for example, the Vanguard® PFR Partial Knee, commercially available from Biomet Manufacturing Corp., Warsaw, Ind. An exemplary PFR implant 50 having a stem 52 for attachment to the patellofemoral compartment of the bone is illustrated in FIG. 1A. The various guiding formations can be in the form of tubular structural elements, such as, for example, conical portions or cylindrical portions with cut-outs or windows, and such that the guiding formations can provide guiding support for drilling holes in the bone with reduced weight and improved visibility.

More specifically, the patient-specific convertible guide 100 is designed during the preoperative plan for the specific patient to guide a first type of arthroplasty selected by the surgeon, but is also capable to be used for and guide a second type of arthroplasty, when the surgeon determines intraoperatively that the second type is indicated based on intraoperative conditions or other intraoperative considerations. In the exemplary embodiment of FIG. 1, the convertible guide 100 can be selectively used either for total knee arthroplasty (TKA) or for a partial knee arthroplasty, such as a patellofemoral (PFR) arthroplasty that replaces only the patellofemoral compartment of the knee joint. Accordingly, the convertible guide 100 can be used intraoperatively for total knee arthroplasty or for partial patellofemoral arthroplasty based on an intraoperative determination by the doctor.

Further, the convertible guide 100 can be used for a patellofemoral arthroplasty even though the preoperative plan calls for patellofemoral arthroplasty and no intraoperative change in plan is envisioned, i.e., when no change from a patellofemoral to total knee arthroplasty is contemplated. In such case, the patient-specific convertible guide 100 can still provide improved alignment guidance that requires fewer intraoperative adjustments than conventional trialing and other patellofemoral (PFR) guides, as described below.

The convertible guide 100 can be attached to the femur using anterior pins through the anterior bores 114. The distal guiding bores 110 can be capped or otherwise obstructed with removable, severable, frangible/breakable covers 120, such that no distal holes are drilled through the distal guiding bores 110, unless the surgeon opts for a total knee arthroplasty procedure, in which case the covers 120 are removed or snapped off or twisted off. A patellofemoral pin hole 122 can be drilled into the femur through the patellofemoral guiding bore 118.

Figure 2:
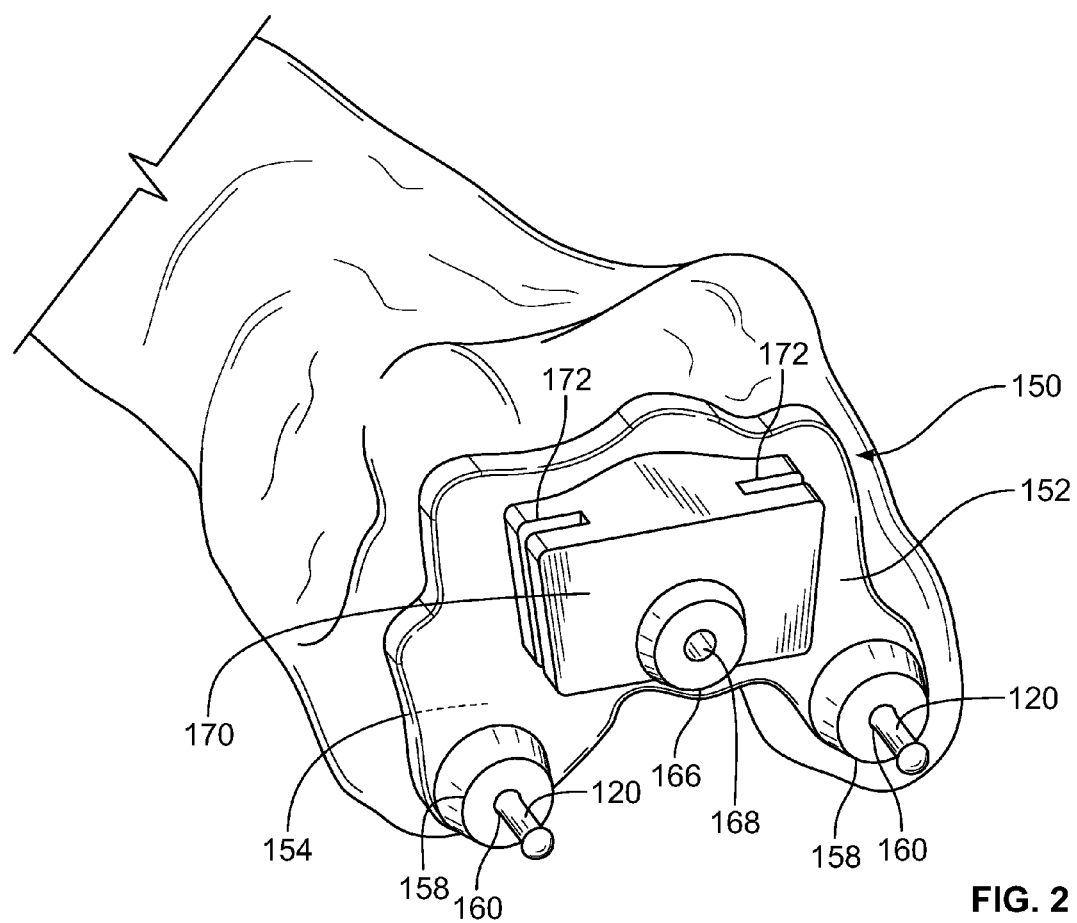
FIG. 2 is a plan view of a patient-specific patellofemoral guide according to the present teachings.

The convertible guide 100 can be removed and a PFR-specific guide 150 can be guided by and pinned on to the femoral bone using the patellofemoral hole 122, as shown in FIG. 2. The PFR guide 150 can be patient-specific and also designed based on the preoperative plan for the specific patient. The PFR guide 150 can include a body 152 having a bone-engagement undersurface 154 that can nestingly mate and conform to the three-dimensional patellofemoral compartment of the patient's distal femur 80. The PFR guide 150 can include two distal guiding formations 158 having distal guiding bores 160 corresponding to the distal guiding bores 110 of the convertible guide 100 and a patellofemoral guiding formation 166 with a patellofemoral bore 168 corresponding to the patellofemoral formation 116 and patellofemoral bore 168 of the convertible guide 100 of FIG. 1. The distal guiding bores 160 can be covered with covers 120, which can be removed, if a TKA procedure is intraoperatively selected by the surgeon instead of the PFR procedure. The PFR guide 150 can also include a supporting structure 170 having first and second slots, openings or other connecting structural features 172 for removably connecting and aligning a femoral resection block 180 (shown in FIG. 4) to the PFR guide 150. In the embodiment illustrated in FIG. 4, the femoral resection block 180 includes first and second legs 182, 184 that can be slidably inserted into the corresponding slots 172 of the PFR guide 150. The femoral resection block 180 can also include a cutting guide 184 for guiding a cutting instrument, such as a blade, to perform an anterior resection. The cutting guide 184 can have a curved or J-shaped profile for wrapping around the medial side of the femur 80 to provide access for the anterior resection. The femoral resection block 180 can also include an aperture 186 for optionally connecting an anterior stylus (not shown), for confirming sizing.

The patient-specific convertible guide 100 and the patient-specific PFR guide 150 are prepared during the preoperative plan so that both are shipped to the surgeon and can be used together. For example, the convertible guide 100 provides all the functions of a patient-specific TKA alignment guide and also includes the additional feature of a PFR guiding formation 116 for drilling the PFR drill hole 122. In this respect, the convertible guide 100 can provide alignment guidance for location or reference pins for use either in a TKA procedure or a partial knee arthroplasty (PKA), such as a PFR procedure. When a TKA procedure is intraoperatively selected, alignment or location pins are placed into the bone through the anterior and distal guiding bores 114, 110 for supporting a distal resection guide, a four-in one cutting block or other cutting block for an anterior resection, chamfer resections, etc., as described in commonly assigned and co-pending U.S. patent application Ser. No. 11/756,057, filed on May 31, 2007, incorporated herein by reference.

Figure 3:
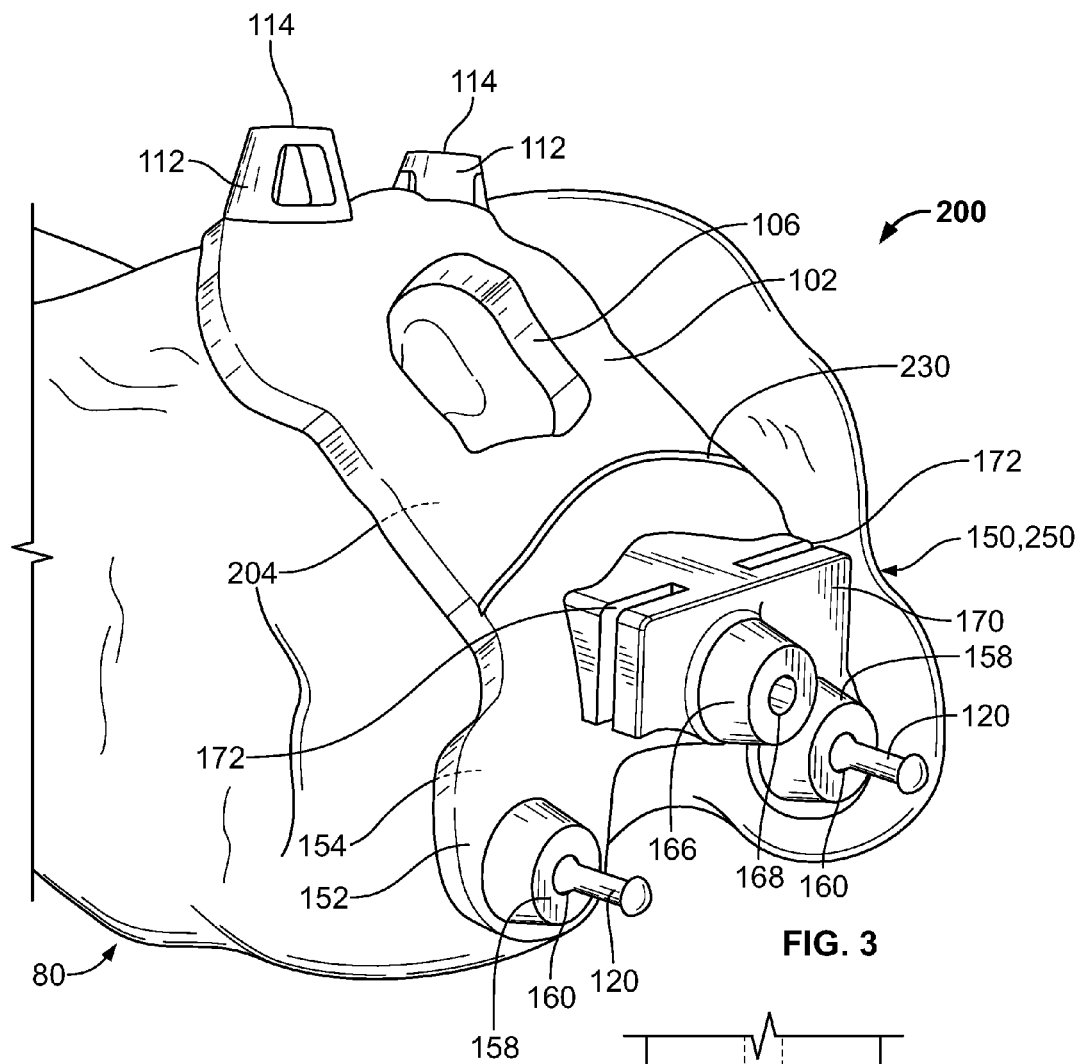
FIG. 3 is an environmental view of a patient-specific convertible guide with an anterior removable section, such that the convertible guide is selectively usable either for a total knee arthroplasty or a patellofemoral procedure as determined intraoperatively by the surgeon according to the present teachings.
Figure 3A:
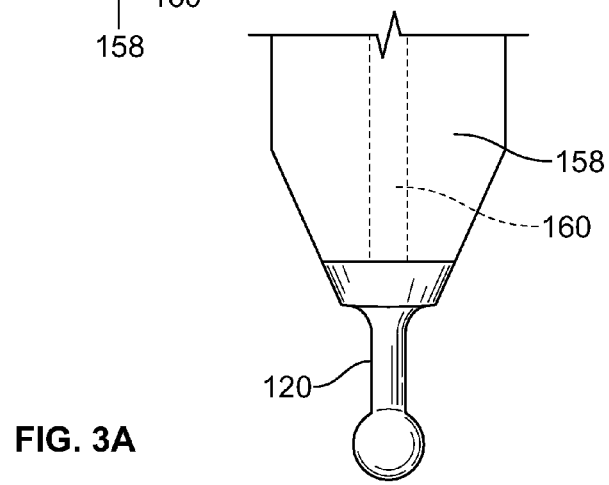
FIG. 3A is a detail of the patient-specific convertible guide of FIG. 3.
Figure 4:
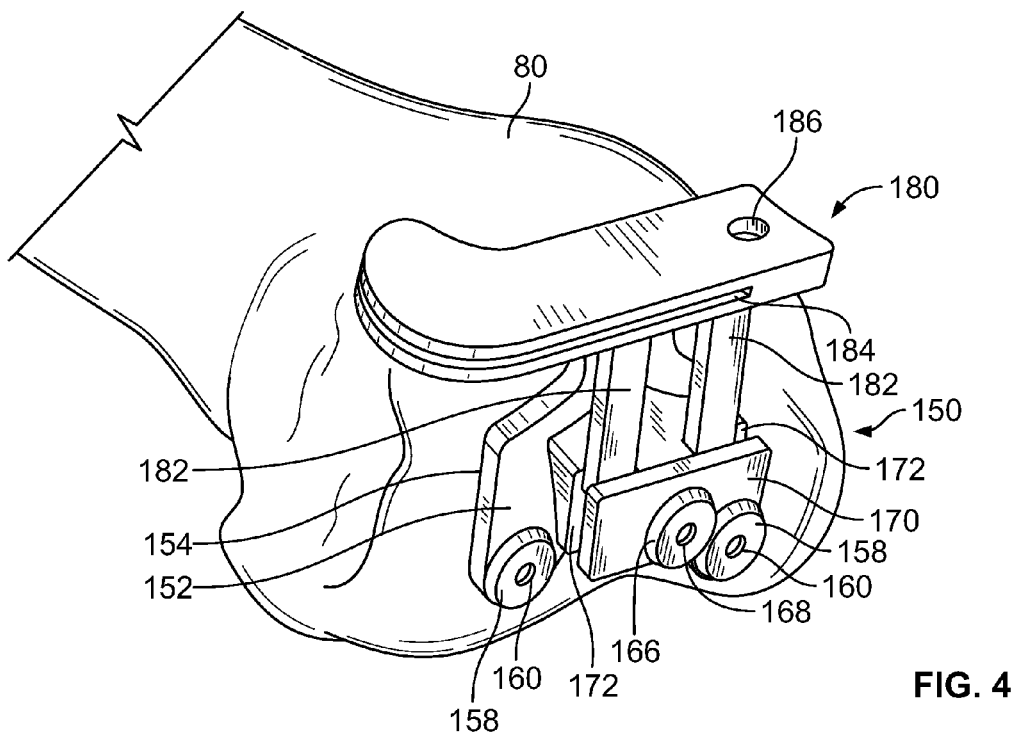
FIG. 4 is the patient-specific convertible guide of FIG. 3 with the anterior section removed and shown with a resection guide according to the present teachings.
Figure 5:
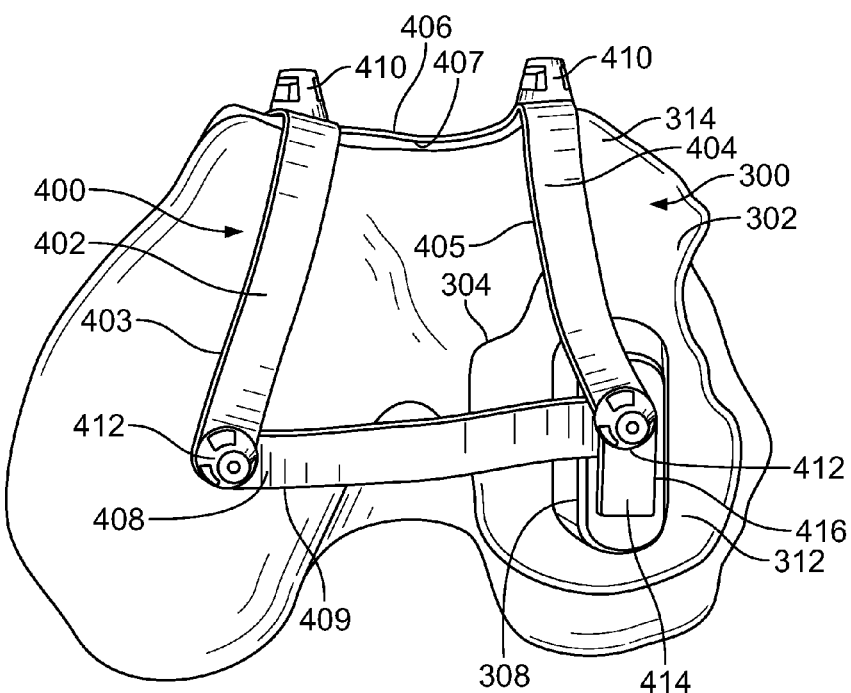
FIG. 5 is an environmental view of a patient-specific guide for partial knee arthroplasty shown with a convertible guide for total knee arthroplasty according to the present teachings.

Referring to FIGS. 3-5, in some embodiments, the functions of convertible guide 100 and PFR guide 150 are incorporated in a single patient-specific convertible guide 200. The same reference numerals are used to denote common elements between the convertible guide 200 and guides 100 and 150. The convertible guide 200 is a frangible, breakable or severable guide with a fracture line or groove or other separator element 230. The separator element 230 facilitates separating a first or anterior portion 202 of the convertible guide 200 from a second portion 250, which, when severed or separated from the first portion 202, defines a standalone, complete guide that is interchangeable with the PFR guide 150 (marked herein with the same numeral numbers as the PFR guide 150). The first portion 202 includes a patient-specific mating undersurface 204 that can be mounted in only one position and mate in a three-dimensional way with the patient's corresponding anatomy. The first portion 202 can include the anterior guiding formations 112 and corresponding bores 114 and the window 106.

The convertible guide 200 provides the surgeon with various options for intraoperative use. For example, in one option, the covers 120 can be removed from the distal guiding bores 160, and the convertible guide 200 can be used as a patient-specific TKA guide providing alignment references and registration for anterior pins through the anterior guiding bores 114 and for distal pins through the distal guiding bores 160. In another option, the convertible guide 200 can be used in a PFR procedure instead of the combination of guides 100 and 150 of FIGS. 1 and 2 discussed above. In this respect, the PFR portion 250/150 can be snapped off either before or after registration to the bone of the patient. For example, the entire convertible guide 200 can be first uniquely mated to the patient's femoral bone 80 and pinned on the femur 80. Then, the first portion 202 can be snapped off and removed, leaving the second portion 250 or PFR guide 150 mounted on the femoral bone 80 to be used with the anterior resection block 180 to perform the anterior resection, as discussed above in reference to FIG. 4. Another option is to snap off the anterior portion 202 before the convertible guide 200 is mounted on the femoral bone 80, such that only the PFR portion 250 or PFR guide 150 is mounted on the femoral bone 80, using the patient-specific undersurface 154 for registration, in view of the fact that the undersurface 154 is designed preoperatively to mate with the corresponding anatomy of the patient in only one position, as discussed above.

Figure 6A:
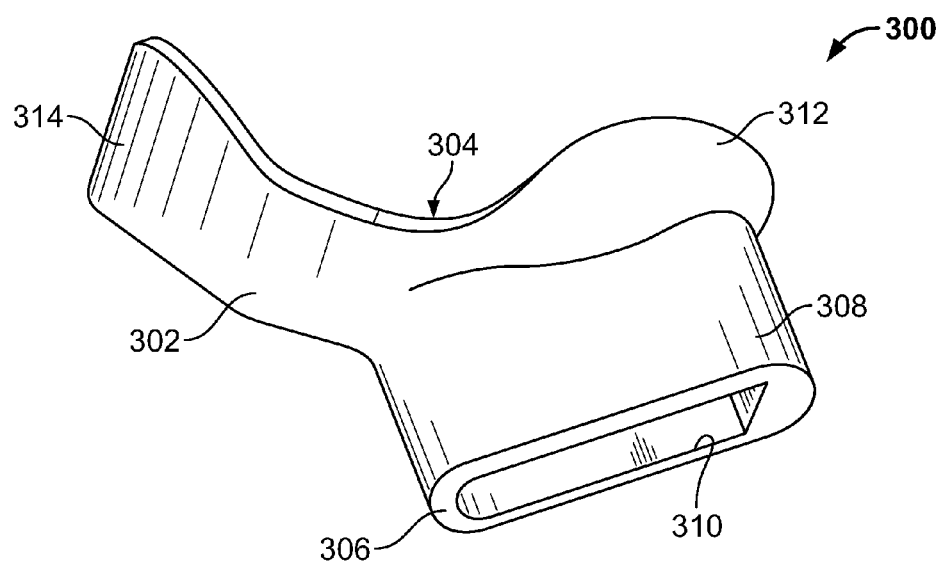
FIG. 6A is a perspective view of a patient-specific guide for partial knee arthroplasty according to the present teachings.
Figure 6C:
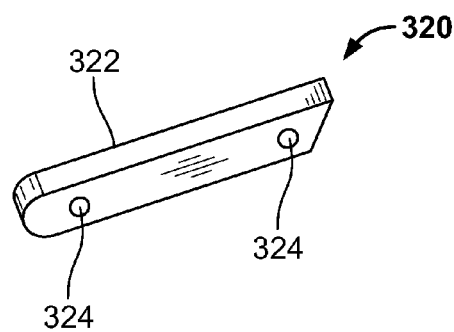
FIG. 6C is a perspective view of a drill template for the patient-specific guide for partial knee arthroplasty of FIG. 6A according to the present teachings.
Figure 6B:
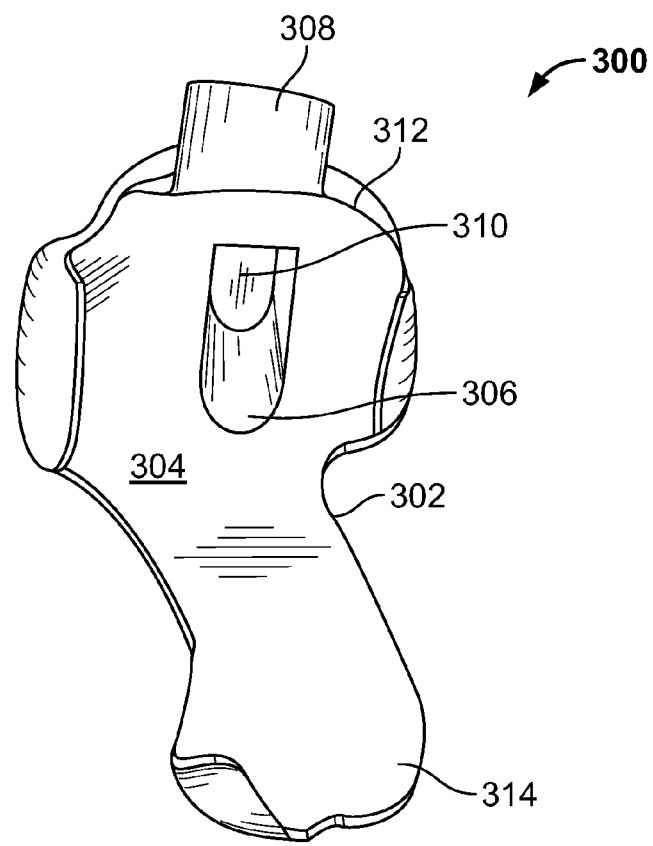
FIG. 6B is another perspective view of the patient-specific guide for partial knee arthroplasty of FIG. 6A.
Figure 6D:
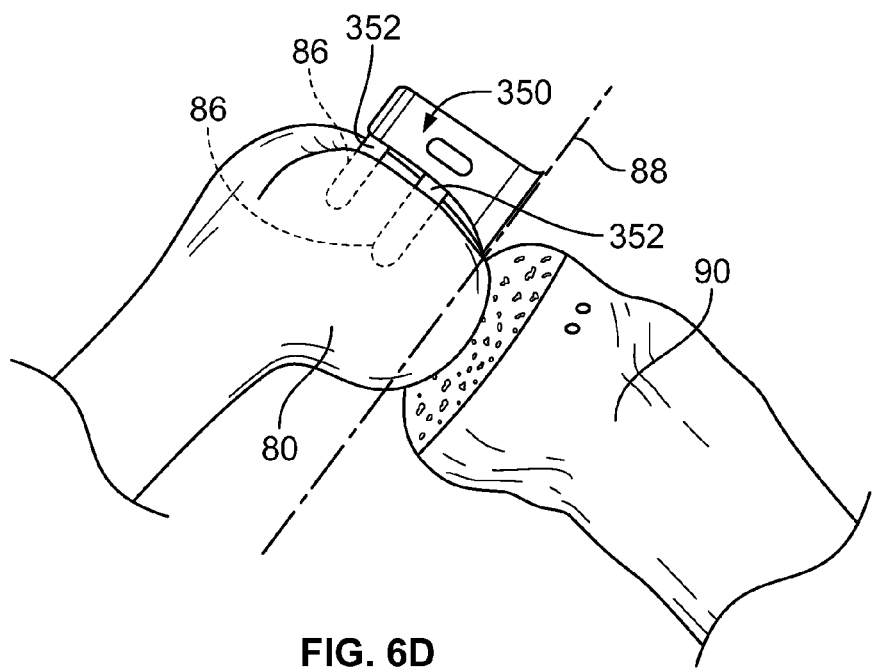
FIG. 6D is an environmental view of a femoral bone with a resection block supported in holes drilled in the bone using the drill template of FIG. 6C according to the present teachings.

Referring to FIG. 5, a patient-specific convertible guide 400 for converting partial (unilateral or unicondylar) knee arthroplasty to total knee arthroplasty is illustrated. The convertible guide 400 can be used with a partial or unilateral or unicondylar femoral guide 300, which can be patient-specific (customized for the patient) or not (standard, non-custom), as shown in FIGS. 6A-6D. The unilateral knee guide 300 illustrated in FIGS. 5, 6A and 6B is patient-specific and includes a body 302 with a three-dimensional patient-specific undersurface 304 designed during the preoperative plan to conform to unilaterally, i.e., to only one of the medial and lateral surfaces/femoral condyles of the femoral bone 80 of the patient in only one position. The body 302 and the undersurface 304 can extend from a distal portion 312 over one of the lateral or medial femoral condyles to an anterior portion 314. The unilateral knee guide 300 can be marked with the name of the patient and the corresponding knee and condyle, such as "RIGHT/MEDIAL", for example, for convenient preoperative and intraoperative identification. A guiding formation 308 extends generally from the distal portion 312. The guiding formation 308 defines an elongated slot 310 with a tapered inner peripheral wall 306. A drill template 320 can be provided for guiding a drill to form one or more holes in the bone as determined during the preoperative plan. An exemplary drill template 320 is illustrated in FIG. 6C in the form of an insert with a tapered peripheral wall 322 that can mate with the inner peripheral wall 306 of the elongated slot 310. The drill template 320 can include a number of guiding holes 324 at a patient-specific location and configuration relative to the unilateral knee guide 300. Two guiding holes 324 are illustrated in FIG. 6C. Depending on the procedure, the surgeon can determine intraoperatively whether to drill corresponding holes 86 in the bone for supporting a resection block 350, as shown in FIG. 6D. In some embodiments, several patient-specific drill templates 320 having different configurations of guiding holes 324 can be provided. The drill templates 320 can be, for example, metallic for added stability, or plastic with sufficient thickness to provide stability.

Intraoperatively, the surgeon can mount the unilateral knee guide 300 on the specified knee and condyle of the patient in a unique position based on the preoperative plan for the patient. If the surgeon determines to proceed with the partial knee procedure, then the drill template 320 can be fitted over the elongated slot 310 and holes 86 for guiding pins can be drilled into the bone 80. The unilateral knee guide 300 can then be removed, and the holes 86 can be used to mount rods or pins 352 of a cutting instrument, such as the resection block 350 illustrated in FIG. 6D, in a position predetermined by the holes 86 drilled in the bone. The resection block 350 is then positioned for performing a resection along a plane 88 for excising the posterior facet of the femoral condyle at a location and orientation determined during the preoperative plan for the patient. The surgical technique can then follow standard procedures, such as, for example, the surgical technique associated with the Oxford® Partial Knee, which is commercially available by Biomet Manufacturing Corp., Warsaw, Ind., and described at Biomet's website.

Alternatively, the surgeon may determine intraoperatively that a total knee arthroplasty (TKA) is indicated instead of the initially planned partial knee arthroplasty (PKA). The convertible guide 400 can then be placed over the already mounted partial knee guide 300 to provide patient-specific registration for a total knee arthroplasty based on the preoperative plan for the patient. The convertible guide 400 is a lightweight guide already sized and shaped for the specific patient in conjunction with the partial knee guide 300. The convertible guide 400 is designed to mate and align with the patient's femoral bone 80 when mounted over the partial knee guide 300 based on the preoperative plan for the patient and in anticipation of a possibility that TKA may be intraoperatively selected instead of the initially planned PKA.

Referring to FIG. 5, in some embodiments, the convertible guide 400 can form a frame of interconnected elongated members including lateral and medial elongated members 402, 404 for the corresponding femoral condyles, an anterior elongated member 406 and a distal elongated member 408. The interconnected elongated members 402, 404, 406, 408 can generally follow and conform the patient's three-dimensional geometry, while their corresponding undersurfaces 403, 405, 407, 409, spatial dimensions and orientations are patient-specific and designed for the anatomy of the specific patient during the preoperative plan. The convertible guide 400 can include guiding formations for TKA pin registration, including anterior guiding formations 410 at connecting portions between the anterior member 406 and the lateral and medial members 402, 404, and distal guiding formations 412 at connecting portions between the distal member 406 and the lateral and medial members 402, 404. The elongated member that is designed to engage the partial knee guide 300, i.e., medial member 404 in the illustration of FIG. 5, includes a connector or extension 414 having a tapered wall 416 that can be received into the elongated slot 310 of the partial knee guide 300 and mate with the tapered inner wall 306 of the slot 310. The corresponding medial distal guiding formation 412 is formed on the extension 414.

The frame structure of the elongated members 402, 404, 406, 408 provides a lightweight and inexpensive addition to the patient-specific kit of a patellofemoral procedure, although a different structure or shape, such as the structure of the patient-specific guides for total knee arthroplasty can be used with the addition of a connector 414.

Figure 7:
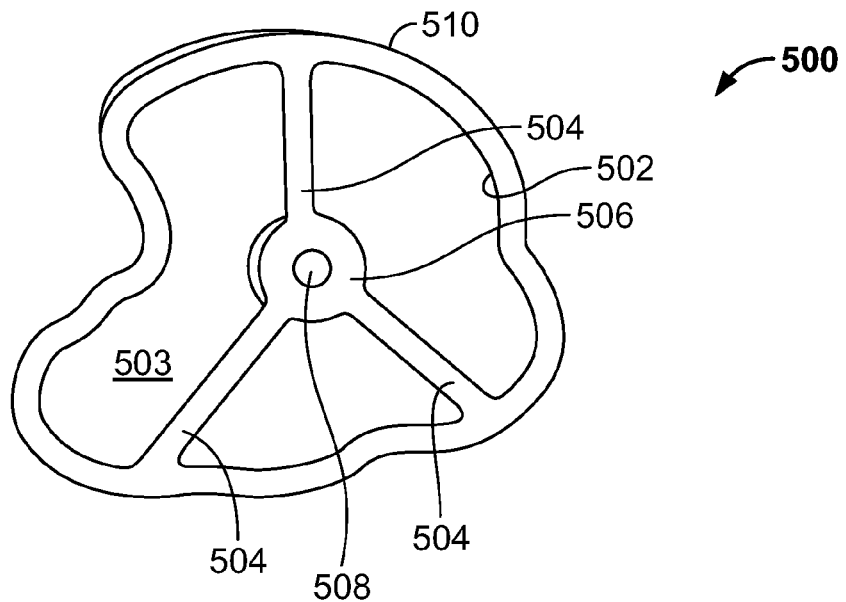
FIG. 7 is a bottom plan view of a patient-specific femoral bone model according to the present teachings.
Figure 8:
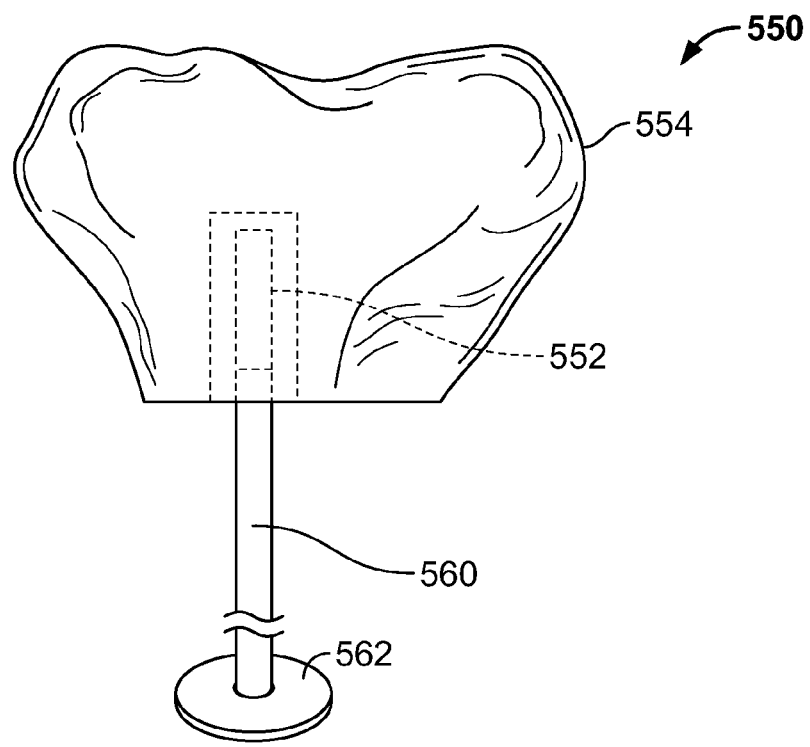
FIG. 8 is an elevated view of a patient-specific tibial bone model according to the present teachings.

Referring to FIGS. 7 and 8, physical (plastic, for example) bone models created as part of the preoperative plan can also be provided to the surgeon in a kit with the patient-specific convertible guides and PFR or PKA guides describe above. The physical bone models have outer three-dimensional surfaces replicating the actual outer bone surfaces of the specific patient and can help the surgeon mount the provided guides thereon and/or visualize the resections and other procedures before mounting the guides on the actual bone of the patient during the operation. These physical bone models can be provided with a support structure that can receive a support element, such as a rod, so that the surgeon can support the physical bone model without directly holding it, thereby providing a full three-dimensional view of the physical bone model. As an example, FIG. 7 illustrates an underside plan view of a physical bone model 500 of the distal femur of a specific patient. The physical bone model 500 has an outer three-dimensional surface 510 that replicates the outer surface of the distal femur of the patient. The support structure includes a central hub 506 supported by a number of arms 504 extending from an inner wall 502 of a hollow underside surface 503 of the bone model 500. The hub 506 can have a blind bore 508 for receiving a holding member, such as the holding member 560 shown in FIG. 8, for holding the bone model with the hollow underside surface 503 facing downwards.

FIG. 8 illustrates a physical bone model 550 for a proximal tibial bone of the specific patient. The physical bone model 550 has an outer three-dimensional surface 554 that replicates the outer surface of the proximal tibia of the patient. The bone model 550 can include a blind bore 552 for receiving a holding member 560 to hold the physical bone for visualization of the resection and other alignment procedures determined during the preoperative plan for the patient. The holding member 560 can be a rod, a bar or other holding structure. The holding member 560 can be held by hand or supported on an appropriate base member 562 on a table or other surface.

The various patient-specific guides, other tools and physical bone models described herein can be manufactured by various stereolithography methods, selective laser sintering, fused deposition modeling or other rapid prototyping methods. In some embodiments, computer instructions of tool paths for machining the patient-specific guides and/or implants can be generated and stored in a tool path data file. The tool path data can be provided as input to a CNC mill or other automated machining system.

The guides and other tools can be made of polymer, ceramic, metal or other suitable material depending on the use, and sterilized as needed. The sterilized tools and bone models can be shipped to the surgeon or medical facility in a kit for a specific patient and surgeon to be used during the surgical procedure.

The various embodiments of patient-specific convertible guides, patellofemoral guides, unilateral/unicondylar guides, drill templates and other instruments can be provided in various combinations to the surgeon and used to facilitate the conversion of a patient-specific preoperative plan from one procedure to another intraoperatively, while retaining the patient-specific guidance provided by the preoperative plan. In this respect, the present teachings integrate preoperatively two different surgical procedures so that either one can be selected intraoperatively as a patient-specific procedure without excessive duplication.

Example embodiments are provided so that this disclosure is thorough, and fully conveys the scope to those who are skilled in the art. Numerous specific details are set forth such as examples of specific components, devices, and methods, to provide a thorough understanding of embodiments of the present disclosure.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of intraoperatively selecting between a partial knee arthroplasty and total knee arthroplasty comprising:
   mounting a patient-specific three-dimensional surface of a convertible patient-specific guide in a unique position mating to a corresponding surface of a distal femoral bone, the patient-specific guide including an anterior portion and a distal portion with a patellofemoral guide portion;
   selecting intraoperatively one of a total knee arthroplasty and a partial knee arthroplasty;
   if total knee arthroplasty is selected, removing first and second covers from corresponding first and second distal guiding bores and registering first and second distal pins through the first and second distal guiding bores; and
   if partial knee arthroplasty is selected, removing the anterior portion along a frangible groove and using the patellofemoral guide portion.

2. The method of claim 1, further comprising registering first and second anterior pins through first and second anterior guiding bores of the anterior portion.

3. The method of claim 1, further comprising supporting a femoral resection block on the patellofemoral guide portion.

4. The method of claim 3, further comprising slidably inserting first and second legs of the femoral resection block into first and second slots of the patellofemoral guide portion.

5. The method of claim 1, wherein the frangible groove has reduced thickness relative to the anterior and distal portions.

6. A method of intraoperatively selecting between a partial knee arthroplasty and total knee arthroplasty comprising:
   providing a convertible patient-specific guide including an anterior portion and a distal portion having a score line of reduced thickness therebetween, the patient-specific guide having a patient-specific three-dimensional undersurface designed preoperatively based on images of a patient's knee joint, the patient-specific three-dimensional undersurface closely mateable in only one position relative to the knee such that the patient-specific three-dimensional undersurface nestingly fits about and within surface portions of a corresponding surface of the knee joint of the patient in a single position;

selecting intraoperatively one of a total knee arthroplasty and a partial knee arthroplasty;

if total knee arthroplasty is selected, mounting the convertible patient-specific guide on the distal femoral bone; and if partial knee arthroplasty is selected, severing and removing the anterior portion along the score line and using the distal portion as a patellofemoral guide.

7. The method of claim 6, wherein the anterior portion is severed and removed before mounting the convertible patient-specific guide on the knee joint.

8. The method of claim 6, wherein the anterior portion is severed and removed after mounting the convertible patient-specific guide on the knee joint.

9. The method of claim 6, further comprising registering anterior and distal pins through corresponding anterior and distal guiding bores and removing covers from the distal guiding bores.

10. The method of claim 6, further comprising:
mounting an anterior femoral resection block on the distal portion; and
making an anterior femoral resection.

11. The method of claim 10, wherein mounting an anterior femoral resection block on the distal portion includes sliding first and second legs of the anterior femoral resection block into corresponding first and second slots of a support extending from the distal portion.

12. A method of intraoperatively selecting between a partial knee arthroplasty and total knee arthroplasty comprising:
providing a convertible patient-specific guide having a first body portion and a second body portion, wherein:
the first body portion has a first patient-specific three-dimensional undersurface custom-made to match an anterior femoral knee joint surface of a specific patient such that the first patient-specific three dimensional-undersurface nestingly fits about and within surface portions of the joint surface in a first position relative to the knee joint;
the second body portion has a second patient-specific three-dimensional undersurface custom-made to match a distal femoral surface of the patient such that the second patient-specific three dimensional-undersurface nestingly fits about and within surface portions of the joint surface in a second position relative to the knee joint;
the first and second patient-specific three-dimensional undersurfaces are constructed from images of the patient's knee joint; and
the second body portion is connected to the first body portion along a frangible line of reduced thickness relative to the first and second body portions;
selecting intraoperatively one of a total knee arthroplasty and a partial knee arthroplasty;
if total knee arthroplasty is selected, mounting the convertible patient-specific guide on the distal femoral bone; and
if partial knee arthroplasty is selected, severing and removing the first body portion along the frangible line and using the second portion as a patellofemoral guide.

13. The method of claim 12, wherein the first body portion is severed and removed before mounting the convertible patient-specific guide on the knee joint.

14. The method of claim 12, wherein the first body portion is severed and removed after mounting the convertible patient-specific guide on the knee joint.

15. The method of claim 12, further comprising registering anterior and distal pins through corresponding anterior and distal guiding bores and removing covers from the distal guiding bores.

16. The method of claim 12, further comprising:
mounting an anterior femoral resection block on the second body portion; and
making an anterior femoral resection.

17. The method of claim 16, wherein mounting an anterior femoral resection block on the second body portion includes sliding first and second legs of the anterior femoral resection block into corresponding first and second slots of a support extending from the second body portion.

18. The method of claim 12, wherein the frangible line is a score line.

19. The method of claim 12, wherein the frangible line is a groove.

20. The method of claim 12, wherein the frangible line is designed preoperatively from the images of the knee joint to correlate the frangible line to a structure of the patient's knee.

* * * * *